United States Patent [19]

Szczepanski

[11] Patent Number: 4,778,889
[45] Date of Patent: Oct. 18, 1988

[54] 2-AMINO-4-HALOGENO-6-CYCLOPROPYL-1,3,5-TRIAZINES

[75] Inventor: Henry Szczepanski, Wallbach, Switzerland

[73] Assignee: Ciba-Geigy Corporation, Ardsley, N.Y.

[21] Appl. No.: 43,720

[22] Filed: Apr. 29, 1987

Related U.S. Application Data

[60] Continuation-in-part of Ser. No. 821,174, Jan. 21, 1986, Pat. No. 4,670,559, which is a continuation-in-part of Ser. No. 693,641, Jan. 22, 1985, which is a division of Ser. No. 535,527, Sep. 26, 1983, Pat. No. 4,515,626.

[30] Foreign Application Priority Data

Jun. 10, 1982 [CH] Switzerland .................. 5874/82

[51] Int. Cl.$^4$ ........................................ C07D 251/16
[52] U.S. Cl. ................................................ 544/211
[58] Field of Search ...................................... 544/211

[56] References Cited

U.S. PATENT DOCUMENTS 4,600,428  7/1986  Szczepanski ............... 544/211
4,655,823  4/1987  Shapiro ..................... 544/211
4,670,559  6/1987  Szczepanski ............... 544/211

Primary Examiner—John M. Ford
Attorney, Agent, or Firm—Kevin T. Mansfield; Edward McC. Roberts

[57] ABSTRACT

2-Amino-4-halogeno-6-cyclopropyl-1,3,5-triazines and a process for this preparation are disclosed.

The 2-amino-4-halogeno-6-cyclopropyl-1,3,5-triazines are intermediates in the production of herbicidally active N-(cyclopropyltriazinyl)-N'-arylsulfonylureas and correspond to the formula I

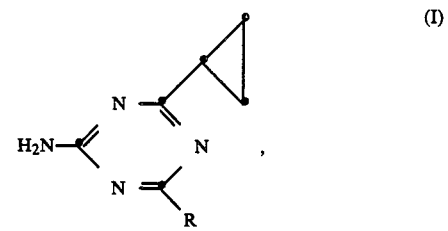

wherein R is halogen.

3 Claims, No Drawings

2-AMINO-4-HALOGENO-6-CYCLOPROPYL-1,3,5-TRIAZINES

The present invention relates to 2-amino-4-halogeno-6-cyclopropyl-1,3-5-triazines and a process for their production. The 2-amino-4-halogeno-6-cyclopropyl-1,3-5-triazines are intermediates in the production of herbicidally active N-(cyclopropyl-1,3,5-triazinyl)-N'-arylsulfonyl ureas.

They correspond to the formula I

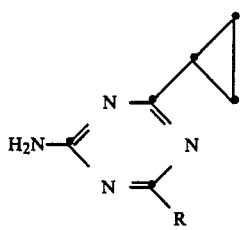

wherein R is halogene.

Some 2-amino-4-cyclopropyl-1,3-5-triazines are known see e.g. 2-amino-4,6-dicyclopropyl-1,3-5-triazine in *Ann* 70 (1067) p. 140–143 or U.K. Pat. No. 1 043 858, compound 12. 4-Amino-2-diallylamino-6-cyclopropylamino in U.S. Pat. No. 3,270,015, example 27.

The 2-amino-4-halogeno-6-cyclopropyl-1,3-5-triazines of formula I are new.

They can be produced by cyclisation of N,N'-dicyano-cyclopropanecarbamidine of formula II as free base or in form of its salts with hydrohalic acid (III)

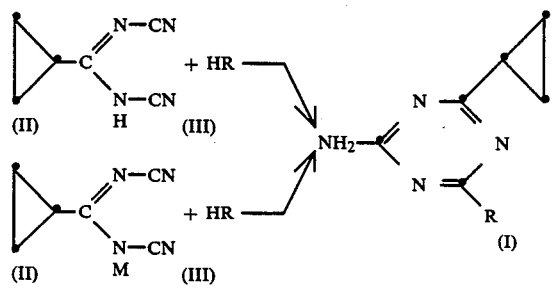

In formula II M stands for an cationic equivalent of an alkali or earthalkali ion.

The compounds of formula I can be used as intermediates for the production of sulfonyl urea of formula (IV) as claimed in the published parent (U.S. Pat. No. 4,515,626) of this application in which formula IV

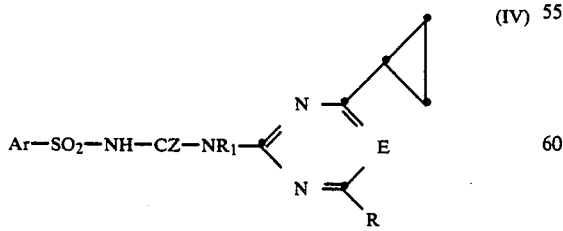

the substituents Ar and Z are as defined in said publication and $R_1$ is hydrogen, E is nitrogen and R is halogen.

The compounds of formula I are preferably used for the production of triazines of formula V

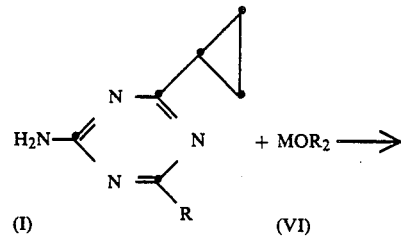

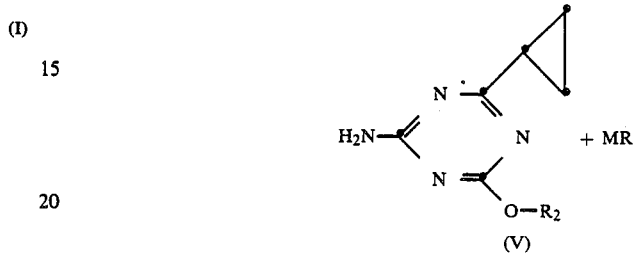

in which process the halogen substituent R in formula I is substituted by the $R_2O$-moiety in formula V by reacting I with an alcohol or an alcoholate of formula VI in which $R_2$ stand for $C_1$–$C_3$-alkyl, $C_1$–$C_3$haloalkyl or $C_2$–$C_6$alkoxyalkyl and M is hydrogen or an equivalent of an alkali- or earthalkali-ion. Compounds of formula V are the subject matter of copending application Ser. No. 821,174 filed Jan. 21, 1986, now U.S. Pat. No. 4,670,559.

This process for the production of 1,3,5-triazines of formula V is a further object of this invention.

The N,N'-dicyano-cyclopropanecarbamidine of formula II and its salts are new compounds they are valuable intermediates for the production of 1,3,5-triazines and are also an object of this invention.

The N,N'-dicyano-cyclopropanecarbamidines of formula II can be prepared starting from cyclopropanecarbonitrile of formula VII which is first converted to the cyclopropanecarbimidic acid ester hydrohalide of formula VIII, in which $R_3$ stands for $C_1$–$C_6$-alkyl, according to the Pinner-method in the presence of a hydrohalic acid HX (X=halogen).

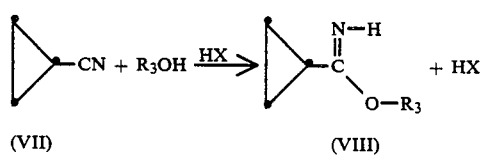

The imidoester (VIII) is then reacted with cyanamide to yield the N-cyanoimidate of formula IX

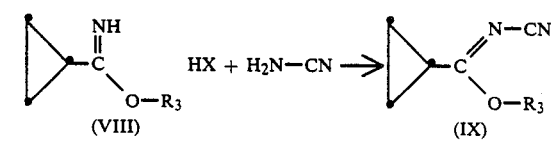

in which $R_3$ is defined as above. In a second reaction step the imidoester IX can be converted to N,N'-dicyano cyclopropane carbamidine of formula II

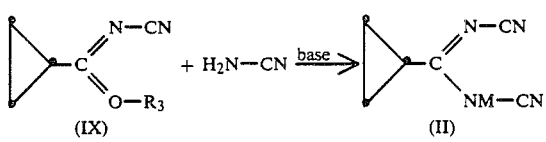

in which M is hydrogen or an equivalent of an alikali or earthalkali ion. This reaction is preferably performed in the presence of a base like an alkali or earthalkali alcoholate to yield compounds of formula II in which M stands for an alkali or earthalkali ion.

The new imidoesters of formula IX and VIII, in which $R_3$ stands for $C_1-C_6$ alkyl (except the imidoesters of formula VIII in which $R_3$ is methyl or ethyl which are known from Chem. Abs. 94 191638 and from U.S. Pat. No. 4,102,910 and U.S. Pat. No. 4,012,506) and their addition salts with hydrohalic acid are a further object of this invention as well as the new amidine of formula II and its salts.

$C_1-C_6$Alkyl used in this description is methyl, ethyl, n-propyl, iso-propyl, n-butyl, iso-butyl, sec-butyl, tert-butyl and the isomeric pentyl and hexylradicals.

The following examples are given to illustrate the invention.

EXAMPLE 1

Cyclopropane carboximide acid methylester hydrochloride

Under stirring and cooling 36,5 g HCl-gas is fed into a solution of 67 g cyclopropane carbonitrile in 42 ml methanol at temperatures between −5° and 0° C.

After 2,5 h 150 ml tetrahydrofuran is added and the solid product is separated and dried.

One isolates 78 g (57,5%) of the title compound of formula

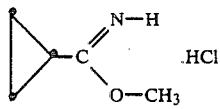

as crystals with a mp. of 111°-114° C.

EXAMPLE 2

N-Cyano-cyclopropanecarboximide acid methylester

A mixture of 27,1 g cyclopropanecarboximidic acid methylester hydrochloride and 8,4 g cyanamide in 100 ml methanole is stirred at 60° C. for 90 min. After adding 100 ml of tetrahydrofurane and cooling at 0° C. the precipitate is filtered off and the filtrate is destilled.

One isolates 22 g (88,6%) of the title compound of formula

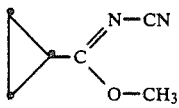

as a colourless oil.

EXAMPLE 3

N,N'-Dicyano-cyclopropanecarbamidine

At 0° C. 8,4 g of cyanamide in 50 ml methanole are added to 36 g of a 30% solution of sodium methylate in methanol and stirred for 30 min. at 10° C. The resulting solution is then cooled to −20° C. and mixed with a solution of 22 g N-cyano-cyclopropanecarboximidic acid methylester in 60 ml methanole. The reaction mixture is then stirred for 30 min. at 20° C. and then evaporated. 100 ml of dioxane is added to the resulting residue which is then concentrated by evaporation. Then again 100 ml of toluene is added and the solution is concentrated at an ambient temperature of 60° C. up to a residual weight of 33 g.

One isolation 33 g of the unpurified sodium salt of formula

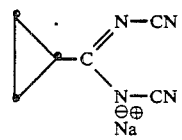

which is used without any further purification.

EXAMPLE 4

2-Amino-4-chloro-6-cyclopropyl-1,3,5-triazine 33 g of the sodium salt of N,N'-dicyano-cyclopropanecarbamidine (rough product) is suspended in 100 ml butanone. A solution of 20 g HCl in 400 ml butanone is dropped under stirring into this solution at 10° C. After the addition has been completed it is stirred for 1 h at ambient temperature. The reaction mixture is concentrated by evaporation and 200 ml of saturated aqueous $NaHCO_3$-solution and 300 ml diethylether are added. The organic phase is separated, washed, dried and concentrated by evaporation. One isolates 21 g of crude product which is treated with hexane to leave the pure title product.

One isolates 20 g of the title compound of formula

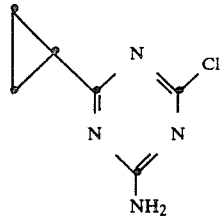

as crystals of mp. 139°-142° C.

EXAMPLE 5

2-Amino-4-ethoxy-6-cyclopropyl-1,3,5-triazine

A freshly prepared solution of sodium ethylate in ethanole (prepared from 1.5 g sodium and 100 ml ethanole) is cooled to 0° C. and mixed with 8,53 g 2-Amino-4-chloro-6-cyclopropyl-1,3,5-triazine. This mixture is kept for 1 h at room temperature and then concentrated by evaporation. To the residue 300 ml of an aqueous 2% $NaHCO_3$-solution are added and then extracted two times with 300 ml of diethylether/dichloromethane (3:2). The organic solvent is then evaporated off.

One isolates 8.7 g of the title compound of formula

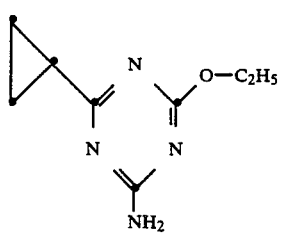

as crystals of mp 111°–113° C.

What is claimed is:

1. 2-Amino-4-halogeno-6-cyclopropyl-1,3,5-triazines of formula I

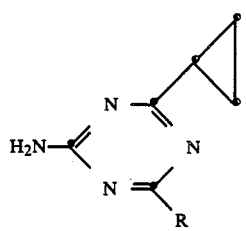

(I)

wherein R is halogen.

2. 2-Amino-4-chloro-6-cyclopropyl-1,3,5-triazine according to claim 1.

3. A process for the preparation of 2-amino-4-halogeno-6-cyclopropyl-1,3,5-triazine of formula I

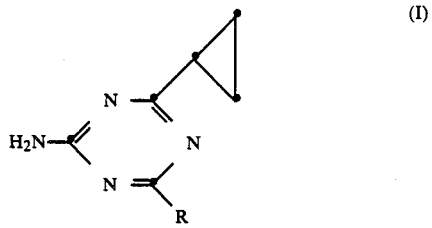

(I)

where R is halogen, which process comprises the cyclisation of a N,N'-dicyano-cyclopropanecarbamidine of formula II

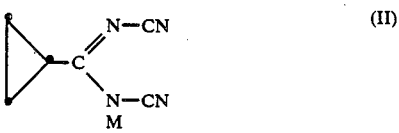

(II)

wherein M is hydrogen or an equivalent of an alkali or earthalkali ion, with hydrohalic acid.

* * * * *

UNITED STATES PATENT AND TRADEMARK OFFICE
CERTIFICATE OF CORRECTION

PATENT NO. : 4,778,889
DATED : October 18, 1988
INVENTOR(S) : Henry Szczepanski

It is certified that error appears in the above-identified patent and that said Letters Patent is hereby corrected as shown below:

On the title page,

Item [30] should read as follows:

-- October 6, 1982 [CH] Switzerland........5874/82 --.

Signed and Sealed this

Ninth Day of May, 1989

*Attest:*

DONALD J. QUIGG

*Attesting Officer*     *Commissioner of Patents and Trademarks*